(12) United States Patent
Mayer et al.

(10) Patent No.: US 7,232,663 B2
(45) Date of Patent: Jun. 19, 2007

(54) ASSAYS EMPLOYING NOVEL SUBSTRATES FOR MEASURING P450-MEDIATED N-DEALKYLATION

(75) Inventors: Gabriele E. Mayer, Laramie, WY (US); E. Kurt Dolence, Laramie, WY (US); Richard T. Mayer, Laramie, WY (US)

(73) Assignees: The University of Wyoming, Laramie, WY (US); The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/180,206

(22) Filed: Jul. 13, 2005

(65) Prior Publication Data

US 2007/0015235 A1 Jan. 18, 2007

(51) Int. Cl.
*C12Q 1/26* (2006.01)
*G01N 33/53* (2006.01)

(52) U.S. Cl. ...................... 435/25; 435/7.72
(58) Field of Classification Search .......... 435/25, 435/7.72
See application file for complete search history.

(56) References Cited

U.S. PATENT DOCUMENTS 6,130,342 A * 10/2000 Miller et al. .......... 549/399

OTHER PUBLICATIONS

Bellec et al.Cytochrome P450 Metabolic Dealkylation of Nine N-nitrosodialkylamines by Human Liver Microsomes; Carcinogenesis, vol. 17, No. 9 (1996) pp. 2029-2034.*
Moller et al. 9-aminoacridine as a Fluorescent Probe of the Electrical Diffuse Layer Associated With the Membranes of Plant Mitochondria; Biochem. J., vol. 193 (1981) pp. 37-46.*
Stresser et al. Cytochrome P450 Fluorometric Substrates: Identification of Isoform-Selective Probes for Rat CYPD2D2 and Human CYP3A4; Drug Metabolism and Disposition, vol. 30, No. 7 (2002) pp. 845-852.*
Carratore et al. Cloning and Expression of Rat CYP2E1 in *Saccharomyces cervisiae:* Detection of Genotoxicityof N-Alkylformamides; Environmental and Molecular Mutagenesis, vol. 36 (2000) pp. 97-104.*
Galy et al. Preparation of a Series of 9-Alkylaminoacridines and 9-Imino-10-Alkylacridines and Their Binding to Desoribonucleic Acid; Arzneimittel-Forschung, vol. 37, No. 10 (1987) pp. 1095-1098.*
Spatzenegger, M. et al., Clinical Importance of hepatic cytochrome P450 in drug metabolism, Drug Metab Rev., 27(3): 397-417 (1995).
Murray, Michael, P450 Enzymes Inhibition Mechanisms. Genetic Regulation and Effects of Liver Disease, Clin. Pharmacokinet, 23(2): 132-146 (1992).
Niwa, T. et al., Contribution of human hepatic cytochrome P450s and steroiodgenic CYP17 to the N-demethylation of aminopyrine, 29(2): 187-93 (1999) [Abstract only].
Chiron, Julien et al., Reactivity of the Acridine Ring: A Review, Synthesis, pp. 313-325 (2004) [Abstract only].
Crespi, Charles L. et al., Microtiter Plate Assays for Inhibition of Human, Drug-Metabolizing Cytochromes P450, Anal. Biochem., 248: 188-190 (1997).
Doostdar, Hamed et al., Bioflavonoids: selective substrates and Inhibitors for cytochrome P450 CYP1A and CYP1B1, Toxicology, 144: 31-38 (2000).
Moody, G.C. et al., Fully automated analysis of activities catalysed by the major human liver cytochrome P450 (CYP) . . . , Xenobiotica, 29(1): 53-75 (1999) [Abstract only].
Stresser, David M et al., Highly Selective Inhibition of Human CYP3A In Vitro by Azamulin and Evidence . . . , Drug Metabolism and Disposition, 32: 105-112 (2004).
Kupfer, David et al., Determination of Enzymic Demethylation of p-Chloro-N-methylaniline.., Anal. Biochem., 17: 502-512 (1966).
Netter, K.J., Naunyn Schmiedebergs Arch Pharmakol Exp Pathol, 255 (2): 151-62 (1966) [Abstract only].
Van der Hoeven, Th., A Sensitive, Fluorometric Method for the Assay of Microsomal Hydroxylase: N-Demethylation . . . , Anal. Biochem., 77: 523-528 (1977).
Yamamoto, T. et al., High-throughput screeening to estimate single or multiple enzymes nlvolved in drug metabolism . . . , Xenobiotioa, 33(8): 823-39 (2003 [Abstract only].

* cited by examiner

*Primary Examiner*—Jon Weber
*Assistant Examiner*—Paul Martin
(74) *Attorney, Agent, or Firm*—Patrick J. Hagan, Esq.; Dann, Dorfman, Herrell and Skillman, P.C.

(57) ABSTRACT

Methods and compositions for measuring N-dealkylating activity of cytochromes P450 enyzmes are disclosed.

12 Claims, 3 Drawing Sheets

ASSAYS EMPLOYING NOVEL SUBSTRATES FOR MEASURING P450-MEDIATED N-DEALKYLATION

FIELD OF THE INVENTION

This invention relates to the field of pharmacology and in particular, drug metabolism. More specifically, the invention provides fluorescent substrates useful for measuring N-dealkylase activity directly in real time.

BACKGROUND OF THE INVENTION

Several research articles and patent documents are cited throughout this application to more fully describe the state of the art to which this invention pertains. The entire disclosure of these citations is incorporated by reference herein as though set forth in full.

Cytochromes P450 are the principal enzymes for the oxidative metabolism of drugs and other xenobiotics. Among the cytochromes P450, five forms, CYP1A2, CYP2C9, CYP2C19, CYP2D6, and CYP3A4, appear to be most commonly responsible for the metabolism of drugs (1). Inhibition or induction of cytochrome P450-mediated metabolism is often the underlying mechanism responsible for drug-drug interactions (2). Such interactions can lead to a substantial decrease or increase in the blood and tissue concentrations of a drug or metabolite. These types of changes can alter a new drug's safety and efficacy profile in important ways, particularly those drugs with a narrow therapeutic range.

The development of sensitive and specific assays for a drug and its metabolite(s) is critical to the study of the drug's metabolism and interactions. For most drugs the metabolizing enzyme(s) is (are) known and chemical inhibitors for the specific enzyme(s) are available. The potential for enzyme inhibition is routinely assessed by performing in vitro inhibition studies using cDNA-expressed enzymes or human liver microsomes. This is done using large through-put studies with known substrates, or HPLC analyses of the metabolites. If inhibition of cytochrome P450 activity is detected, predictions of potential side effects can be made. Accurate measurement of inhibition can be performed in either in vivo or in vitro systems containing the specific cytochrome P450, a substrate and a putative inhibitor. Many cytochrome P450 enzymes are commercially available. Inhibitors of P450 enzymes are currently known, however, suitable N-dealkylase substrates for massive through-put studies are scarce.

Moody et al. (Xenobiotica 29: 53–75 (1999)) describe automated inhibition screens for the major human hepatic cytochromes P450. Radiometric analysis of erythromycin N-demethylation forg CYP3A4, dextromethorphan O-demethylation for CYP2D6, naproxen O-demethylation for CYP2C9 and diazepam N-demethylation for CYP2C19 were employed. For the radiometric assays greater than 99.7% of $^{14}$C-labelled substrate was routinely extracted from incubations by solid-phase extraction.

Stresser et al. (Drug Metabolism and Disposition 32:105–112 (2004)) tested azamulin, an anti-infective toward 18 different cytochromes P450 using human liver microsomes or microsomes from insect cells expressing single isoforms. The products from these chemical reactions were determined using HPLC analyses which are time consuming and labor intensive.

SUMMARY OF THE INVENTION

In accordance with the present invention, new substrates for cytochrome P450 enzymes and methods of use thereof have been developed. These substrates and methods facilitate assessing the effects of new drugs on cytochrome P450 enzyme action. Additionally, the substrates described herein may be used to advantage for evaluating a drug's potential for enzyme inhibition and/or induction. An exemplary method entails determining N-dealkylase activity of a cytochrome P450 enzyme by exposing an 9-N-alkylacridine to the enzyme under conditions suitable for catalysis to occur followed by measuring production of 9-aminoacridine.

In another aspect, the method includes adding a test agent during the incubation to determine the effect of the agent on the production of 9-aminoacridine. There are many cytochrome P450 enzymes that can be tested using the methods of the invention. These include, without limitation, CYP1A2, CYP2C8, CYPC18, CYP2C19, CYP2D6, CYP3A4, CYP1A1.

Cytochrome P450 activity can be assessed using purified enzyme in vitro, in a liver microsome preparation or in whole cells expressing at least one cytochrome P450 enzyme.

In yet a further aspect of the invention, a 9-N-alkylacridine is provided selected from the group consisting of 9-N-(methylamino)acridine, 9-N-(ethylamino)acridine, 9-N-(1-aminopropyl)acridine, 9-N-(1-aminobutyl)acridine, and 9-N-(1-aminopentyl)acridine.

DETAILED DESCRIPTION OF THE INVENTION

Figure 1:
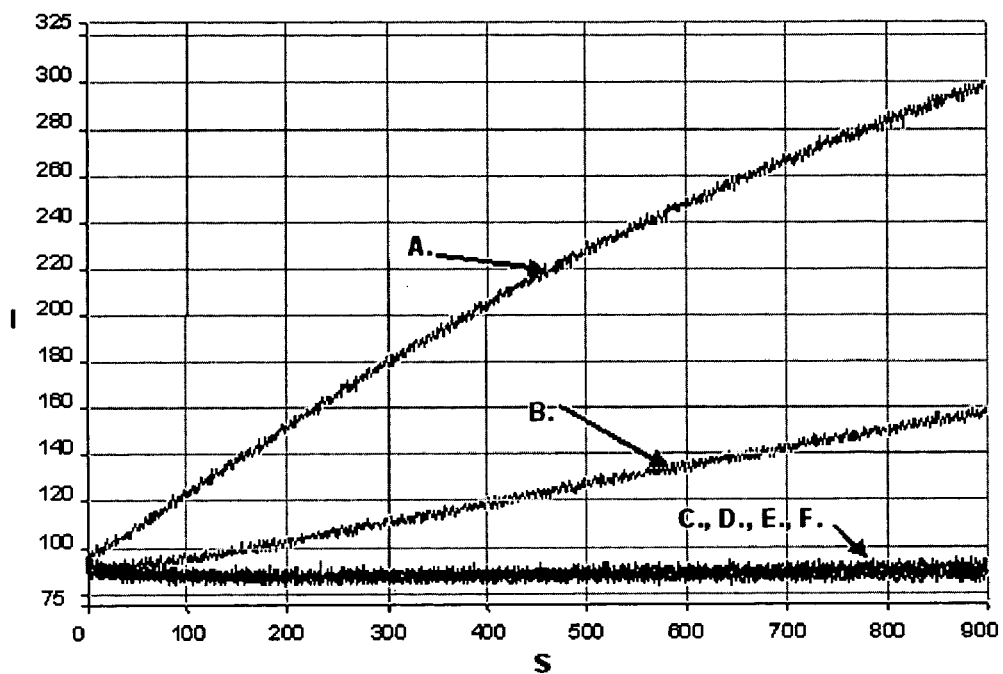
FIG. 1 is a graph showing the relative activities of various CYP's with 9-N-methylaminoacridine. Reactions contained 8 pmoles of CYP, 5 µM 9-N-(methylamino)acridine, 250 µM NADPH, in a total volume of 2 ml of 100 mM potassium phosphate buffer, pH 7.2. A. CYP2D6; B. CYP1A1; C. CYP3A4; D. CYP3A5; E. CYP1A2; F. CYP2C19; I=Fluorescence Intensity; S=Seconds.

Many drugs are basic compounds with regard to pH, containing one or more nitrogen atoms that may or may not have alkyl groups attached. Some well-known examples include stimulants, opiates, and antidepressant drugs. If the nitrogen is located in a side chain, these compounds are frequently N-dealkylated by cytochromes P450 early in the metabolic process. The major enzymes responsible for N-dealkylation are CYP2C19, CYP2C8, CYP2D6, CYPC18, CYP1A2, and CYP3A4 (3). To assess drug metabolism by one or more of these enzymes, in vitro inhibition studies are performed using cDNA expressed enzymes and specific substrates. Currently few direct, facile assays are available to directly measure the N-dealkylating power of these enzymes. Commonly used assays include aminopyrine and mephenytoin N-dealkylation. These assays require several steps before the product can be determined. A more practical assay would be one that is simple and direct, requiring no preparative or subsequent purification steps. Ideal substrates would be those having enzymatic products that are significantly different with regard to spectrophotometric (spectral) characteristics when compared to the substrates per se.

To this end, a series of 9-N-alkylaminoacridines (methyl-, ethyl-, propyl-, butyl-, and pentyl-aminoacridine) have been synthesized. Acridine derivatives are known to be potent biological fluorescent probes (4). The 9-N-alkylaminoacridine substrates and the predicted metabolite, 9-aminoacridine, are fluorescent but differ significantly in their quantum yields (15- to 20-fold). The quantum yield and spectral differences should allow quantitation of product from substrates. Substrates may be tested with CYP3A4, CYP3A5, CYP2C19, CYP1A2, CYP1A1, and CYP2D6. The N-dealkylating activities of these enzymes towards the acridines can be determined using assays similar to those developed by Crespi et al. (5) and Doostdar et al. (6). Several of these acridines are expected to act as specific substrates for N-dealkylating enzymes. Additionally, N-dealkylation reactions involving these substrates can be performed in real-time making this an easily determined parameter for cytochrome P450 enzyme activity. Finally, the reactions can be performed in the presence of a test agent to ascertain its ability to modulate catalysis mediated by cytochrome P450 enzymes. Such agents, include, without limitation, beta adrenergic blockers (e.g., carvedilol, metoprolol, propranolol), antidepressants (e.g., amitriptyline, desipramine, imipramine), antipsychotic agents (e.g., haloperidol, perphenazine, thioridazine), dextromethorphan, codeine, lidocaine, tamoxifen, methamphetamine, herbal natural products (e.g., St. John's wort, milk thistle, other bioflavinoids) and many other classes of drugs.

The following examples are provided to illustrate various embodiments of the invention. They are not intended to limit the invention in any way.

EXAMPLE I

Synthesis of 9-N-(methylamino)acridine free amine

9-N-(Methylamino)acridine is prepared by the following reaction (Scheme I), the details of which are described herein below.

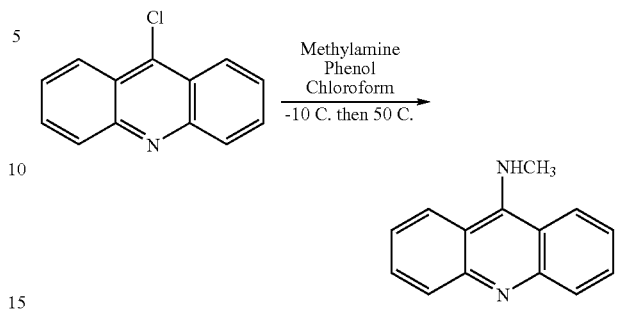

Scheme I

Anhydrous phenol (22.0 g, 234.1 mmoles) was placed into a 250 mL 3-neck round bottom flask equipped with a magnetic stirring bar, reflux condenser, thermometer, dry ice/acetone condenser and positive pressure nitrogen source. Anhydrous chloroform (100 mL) was added and the mixture stirred and cooled in a sodium chloride ice bath until the internal temperature was −10° C. The dry ice condenser was filled with acetone and dry ice while using caution that the system remained under a positive atmosphere of nitrogen. Methylamine gas flow was slowly initiated resulting in condensation of the gas to a liquid and this process was continued until the phenol/chloroform solution was saturated. Saturation was determined by initiation of refluxing of methylamine upon removal of the cooling bath. To this solution at an internal temperature of −10° C. was added dropwise using an addition funnel a solution of 9-chloroacridine (5.0 g, 23.4 mmoles) in 25 mL of anhydrous chloroform. This was followed by another 25 mL anhydrous chloroform to complete the addition. The reaction mixture was stirred for 1 hour at −10° C. then warmed to room temperature and stirred for 2 hours. During this ambient temperature stirring the dry ice acetone condenser was kept full to help prevent escape of the methylamine from the reaction vessel. At the end of this 2 hour period the solution was slowly warmed to an internal temperature of 50–55° C. using an oil bath. The mixture was maintained at this temperature overnight. Sampling of the reaction mixture and analysis by gas chromatography/mass spectroscopy indicated the absence of starting 9-chloroacridine ($t_R$=6.4 minutes) and the appearance of a new peak at $t_R$=7.5 minutes corresponding to the desired product. This GC/EI-MS was obtained on an Agilent model 6890 and 5973 instrument and an Agilent Technologies HP-5MS 30 m×0.25 mm 0.25 μm capillary column utilizing the following temperature run profile: Starting at 150° C. for 1 minute then ramping at 25° C. per minute to 300° C. and holding for 4 minutes.

The reaction mixture was cooled to room temperature and transferred to a 500 mL separatory funnel with the aid of 50 mL of chloroform. This solution was washed with 100 mL of 13% aqueous sodium hydroxide solution. This aqueous phase was extracted with 100 mL choroform. The pooled organic phases were washed with one 100 mL portion of 10% aqueous sodium hydroxide and two 100 mL portions of saturated aqueous sodium chloride solution, then dried over solid anhydrous sodium sulfate and finally filtered through a bed of sodium sulfate. This solution was concentrated to dryness by rotary evaporation to afford a yellow/brown solid. The solid was dissolved in 200 mL of boiling hot anhydrous acetonitrile and left to cool under a nitrogen environment at ambient room temperature resulting in crystallization. The solid was collected by suction filtration and washed with hexanes. The mother liquor was concentrated and a second crop of crystals obtained similar to that described above. The solid material was dried under high vacuum overnight to afford 4.431 grams (91% yield) of a yellow powder as the free base.

Characterization data: MP 172–173° C. (uncorrected); GC/EI-MS $t_R$=7.47 minutes; m/z 208; $^1$H NMR (CDCl$_3$) δ 8.13 (d, 2H, J=8.8 Hz, aromatic), 8.03 (d, 2H, J=8.7 Hz, aromatic), 7.62 (t, 2H, J=7.1 and 8.1 Hz, aromatic), 7.29 (t, 2H, J=7.4 and 8.0 Hz, aromatic), 5.72 (br s, 1H, NH), 3.51 (s, 3H, CH$_3$); $^{13}$C NMR (CDCl$_3$) δ 151.93, 149.12, 129.77, 128.93, 122.85, 122.47, 115.82, 37.44; Anal. Calcd for C$_{14}$H$_{12}$N$_2$ (208): C, 80.74; H, 5.81; N, 13.45. Found: C, 80.09; H, 5.84; N, 13.22.

EXAMPLE 2

Synthesis of 9-N-(ethylamino)acridine free amine

9-N-(Ethylamino)acridine free amine was prepared by the following reaction (Scheme II), the details of which are provided hereinbelow.

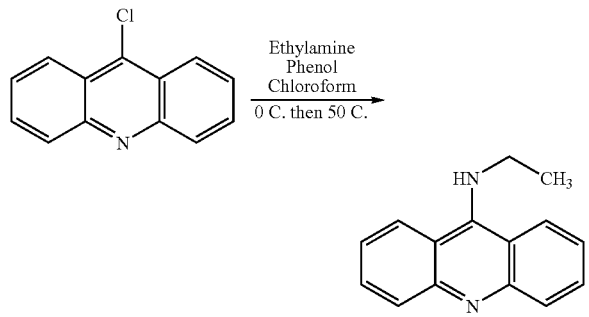

Scheme II

Anhydrous phenol (22.0 g, 234.1 mmoles) was placed into a 250 mL 3-neck round bottom flask equipped with a magnetic stirring bar, reflux condenser, thermometer, dry ice/acetone condenser and positive pressure nitrogen source. Anhydrous chloroform (50 mL) was added and the mixture stirred and cooled in an ice bath until the internal temperature was 0° C. The dry ice condenser was filled with acetone and dry ice while using caution that the system remained under a positive atmosphere of nitrogen. Ethylamine gas flow was slowly initiated resulting in condensation of the gas to a liquid and this process was continued until the phenol/chloroform solution was saturated. Saturation was determined by initiation of refluxing of ethylamine upon removal of the cooling bath. To this solution at an internal temperature of 0° C. was added dropwise using an addition funnel a solution of 9-chloroacridine (5.0 g, 23.4 mmoles) in 25 mL of anhydrous chloroform. This was followed by another 25 mL of anhydrous chloroform to complete the addition. The cooling bath was removed and the reaction mixture was stirred while warming to room temperature. Stirring was continued for 3 hours at ambient temperature. During this ambient temperature stirring the dry ice acetone condenser was kept full to help prevent escape of the ethylamine from the reaction vessel. The solution was slowly warmed to an internal temperature of 50–55° C. using an oil bath. The mixture was maintained at this temperature overnight. Sampling of the reaction mixture and analysis by gas chromatography/mass spectroscopy indicated the absence of starting 9-chloroacridine ($t_R$=6.4 minutes) and the appearance of a new peak at $t_R$=7.6 minutes corresponding to the desired product. This GC/EI-MS was obtained on an Agilent model 6890 and 5973 instrument and an Agilent Technologies HP-5MS 30 m×0.25 mm 0.25 μm capillary column utilizing the following temperature run profile: Starting at 150° C. for 1 minute then ramping at 25° C. per minute to 300° C. and holding for 4 minutes.

The reaction mixture was cooled to room temperature and transferred to a 500 mL separatory funnel with the aid of 100 mL of chloroform. This solution was washed with 100 mL of 13% aqueous sodium hydroxide solution. This aqueous phase was extracted with 100 mL choroform. The pooled organic phases were washed with one 100 mL portion of 10% aqueous sodium hydroxide and two 100 mL portions of saturated aqueous sodium chloride solution, then dried over solid anhydrous sodium sulfate and finally filtered through a bed of sodium sulfate. This solution was concentrated to dryness by rotary evaporation to afford a brown solid. The solid was dissolved in 200 mL of boiling hot anhydrous acetonitrile and left to cool under a nitrogen environment at room temperature followed by storage in the freezer resulting in crystallization. The solid was collected by suction filtration and washed with hexanes. The solid material was dried under high vacuum for 24 hours to afford 4.525 grams (87% yield) of a brown solid as the free base.

Characterization data: MP 126–127° C. (uncorrected); GC/EI-MS $t_R$=7.55 minutes; m/z 222; $^1$H NMR (CDCl$_3$) δ 8.04–8.08 (m, 4H, aromatic), 7.63 (t, 2H, J=7.6 Hz, aromatic), 7.31 (t, 2H, J=7.5 and 7.7 Hz, aromatic), 5.22 (br s, 1H, NH), 3.79 (q, 2H, J=14.2 Hz, NCH$_2$CH$_3$), 1.34 (t, 3H, J=7.11 Hz, NCH$_2$CH$_3$); $^{13}$C NMR (CDCl$_3$) δ 151.07, 149.14, 129.74, 129.20, 122.81, 122.68, 116.46, 45.31, 16.75; Anal. Calcd for C$_{15}$H$_{14}$N$_2$ (222): C, 81.05; H, 6.35; N, 12.60. Found: C, 81.07; H, 6.33; N, 12.47.

EXAMPLE 3

Synthesis of 9-N-(1-aminopropyl)acridine hydrochloride

9-N-(1-aminopropyl)acridine hydrochloride is prepared by the following reaction (Scheme III), the details of which are provided hereinbelow.

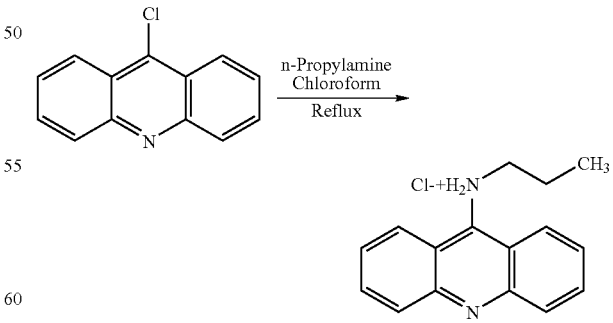

Scheme III

To a 250 mL 3-neck round bottom flask equipped with a magnetic stirring bar, reflux condenser, and positive pressure nitrogen source was added n-propylamine (9.7 mL, 117.0 mmoles) and 100 mL anhydrous chloroform. Using an addition funnel, a solution of 9-chloroacridine (5.0 g, 23.4 mmoles) in anhydrous chloroform (50 mL) was added dropwise. A second 50 mL portion of anhydrous chloroform was used to complete the transfer. The solution was briskly refluxed over a period of 5 days with daily monitoring for consumption of the 9-chloroacridine by GC/EI-MS. Slowly, a new peak at $t_R$=7.9 minutes corresponding to the desired product appeared with slow disappearance of the 9-chloroacridine ($t_R$=6.4 minutes). This GC/EI-MS was obtained on an Agilent model 6890 and 5973 instrument and an Agilent Technologies HP-5MS 30 m×0.25 mm 0.25 μm capillary column utilizing the following temperature run profile: Starting at 150° C. for 1 minute then ramping at 25° C. per minute to 300° C. and holding for 4 minutes.

After 5 days of refluxing all the 9-chloroacridine had been consumed. The solution was cooled to room temperature while under a nitrogen environment and the chloroform removed by rotary evaporation leaving a solid. This solid was dissolved in a minimal amount of hot absolute ethanol and anhydrous diethylether was added to the cloud point. At this time, 25 mL of hexanes were added and the flask was sealed by a rubber septa and placed in the freezer overnight. In the morning, a yellow solid was collected by suction filtration and washed with hexanes followed by drying under high vacuum for 24 hours. This afforded 4.9 g (77% yield) of a yellow solid as the hydrochloride salt.

Characterization data: MP 248–249° C. (uncorrected); GC/EI-MS $t_R$=7.91 minutes; m/z 236 (free amine); $^1$H NMR ($D_2O$, referenced to HDO at 4.80 ppm) δ 7.35–7.40 (m, 4H, aromatic), 6.98 (t, 2H, J=7.6 Hz, aromatic), 6.74 (d, 2H, J=8.6 Hz, aromatic), 3.19 (t, 2H, J=7.2 and 7.9 Hz, NC$\underline{H}_2$CH$_2$CH$_3$), 1.44–1.52 (m, 2H, NCH$_2$C$\underline{H}_2$CH$_3$), 0.85 (t, 3H, J=7.3 Hz, NCH$_2$CH$_2$C$\underline{H}_3$); $^{13}$C NMR ($D_2O$, external referenced to 1,4-dioxane at 66.65 ppm) δ 154.86, 137.66, 134.86, 123.64, 117.44, 110.35, 49.85, 22.64, 10.32; Anal. Calcd for $C_{16}H_{17}N_2Cl_1$ (272): C, 70.45; H, 6.28; N, 10.27. Found: C, 70.58; H, 6.37; N, 10.07.

EXAMPLE 4

Synthesis of 9-N-(1-aminobutyl)acridine hydrochloride

9-N-(1-aminobutyl)acridine hydrochloride is prepared by the following reaction (Scheme IV), the details of which are provided hereinbelow.

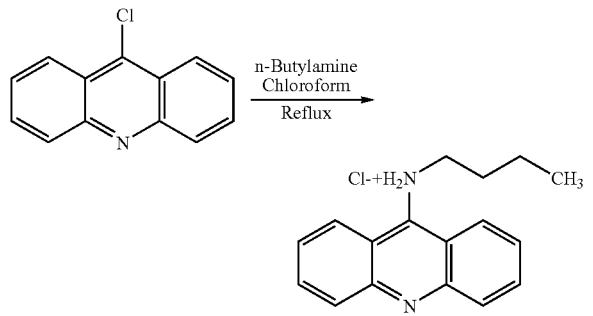

Scheme IV

To a 250 mL 3-neck round bottom flask equipped with a magnetic stirring bar, reflux condenser, and positive pressure nitrogen source was added n-butylamine (11.5 mL, 117.0 mmoles) and 100 mL anhydrous chloroform. Using an addition funnel, a solution of 9-chloroacridine (5.0 g, 23.4 mmoles) in anhydrous chloroform (50 mL) was added dropwise. A second 50 mL portion of anhydrous chloroform was used to complete the transfer. The solution was briskly refluxed over a period of 4 days with daily monitoring for consumption of the 9-chloroacridine by GC/EI-MS. Slowly, a new peak at $t_R$=8.3 minutes corresponding to the desired product appeared with slow disappearance of the 9-chloroacridine ($t_R$=6.4 minutes). This GC/EI-MS was obtained on an Agilent model 6890 and 5973 instrument and an Agilent Technologies HP-5MS 30 m×0.25 mm 0.25 μm capillary column utilizing the following temperature run profile: Starting at 150° C. for 1 minute then ramping at 25° C. per minute to 300° C. and holding for 4 minutes.

After 4 days of refluxing all the 9-chloroacridine had been consumed. The solution was cooled to room temperature while under a nitrogen environment and the chloroform removed by rotary evaporation leaving a dark amber solid. This solid was dissolved in a minimal amount of hot absolute ethanol (20 mL) and anhydrous diethylether (100 mL) and hexanes (100 mL) were added. The flask was sealed by a rubber septa and placed in the freezer overnight. In the morning, a yellow solid was collected by suction filtration and washed with hexanes followed by drying under high vacuum for 48 hours. This afforded 4.5 g (66% yield) of a yellow solid as the hydrochloride salt.

Characterization data: MP 188–190° C. (uncorrected); GC/EI-MS $t_R$=8.30 minutes; m/z 250 (free amine); $^1$H NMR ($D_2O$, referenced to HDO at 4.80 ppm) δ 7.10–7.30 (m, 4H, aromatic), 6.84 (t, 2H, J=7.4 Hz, aromatic), 6.58 (d, 2H, J=8.2 Hz, aromatic), 2.99 (t, 2H, J=7.6 and 7.8 Hz, NC$\underline{H}_2$CH$_2$CH$_2$CH$_3$), 1.26–1.34 (m, 2H, NCH$_2$C$\underline{H}_2$CH$_2$CH$_3$), 1.13–1.21 (m, 2H, NCH$_2$CH$_2$C$\underline{H}_2$CH$_3$), 0.79 (t, 3H, J=7.3 Hz, NCH$_2$CH$_2$CH$_2$C$\underline{H}_3$); $^{13}$C NMR ($D_2O$, external referenced to 1,4-dioxane at 66.65 ppm) δ 154.31, 137.44, 134.79, 123.61, 117.36, 110.04, 49.96, 31.06, 19.32, 12.88; Anal. Calcd for $C_{17}H_{19}N_2Cl_1$ (286): C, 71.19; H, 6.67; N, 9.76. Found: C, 71.03; H, 6.81; N, 9.66.

EXAMPLE 5

Synthesis of 9-N-(1-aminopentyl)acridine free amine

9-N-(1-aminopentyl)acridine is prepared by the following reaction Scheme V), the details of which are provided hereinbelow.

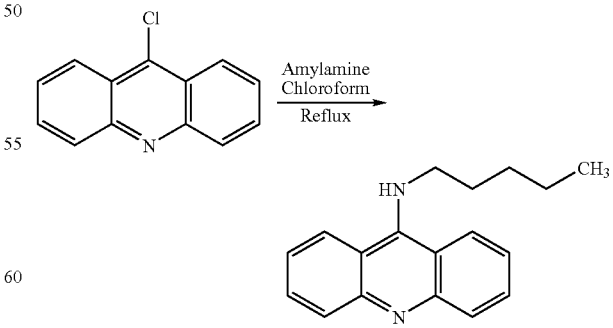

Scheme V

To a 250 mL 3-neck round bottom flask equipped with a magnetic stirring bar, reflux condenser, and positive pressure nitrogen source was added amylamine (13.6 mL, 117.0 mmoles) and 100 mL anhydrous chloroform. Using an addition funnel, a solution of 9-chloroacridine (5.0 g, 23.4 mmoles) in anhydrous chloroform (50 mL) was added dropwise. A second 50 mL portion of anhydrous chloroform was used to complete the transfer. The solution was briskly refluxed over a period of 6 days with daily monitoring for consumption of the 9-chloroacridine by GC/EI-MS. Slowly, a new peak at $t_R$=8.8 minutes corresponding to the desired product appeared with slow disappearance of the 9-chloroacridine ($t_R$=6.4 minutes). This GC/EI-MS was obtained on an Agilent model 6890 and 5973 instrument and an Agilent Technologies HP-5MS 30 m×0.25 mm 0.25 µm capillary column utilizing the following temperature run profile: Starting at 150° C. for 1 minute then ramping at 25° C. per minute to 300° C. and holding for 4 minutes.

After 6 days of refluxing all the 9-chloroacridine had been consumed. The solution was cooled to room temperature while under a nitrogen environment and the chloroform removed by rotary evaporation leaving a semi-solid. This semi-solid resisted crystallization using mixtures of ethanol, diethylether and hexanes. This solution was transferred to a separatory funnel and washed with 0.25 M aqueous potassium hydroxide solution. The aqueous phase was extracted with chloroform (200 mL) and the pooled organic phases washed with 200 mL of saturated aqueous sodium chloride solution. The organic phase was dried over anhydrous sodium sulfate, filtered and evaporated to afford a brown solid. This brown solid was dissolved in a minimum of hot anhydrous acetonitrile, sealed with a rubber septum and allowed to cool at room temperature to afford large brown prism shaped crystals. Storage in the freezer overnight completed crystallization. The solid was collected by suction filtration, washed with hexanes, dried for 24 hours under high vacuum to afford 5.3 g (85% yield) of a brown solid as the free amine.

Characterization data: MP 107–108° C. (uncorrected); GC/EI-MS $t_R$=8.78 minutes; m/z 264 (free amine); $^1$H NMR (CDCl$_3$) δ 8.07 (d, 4H, J=9.0 Hz, aromatic), 7.65 (t, 2H, J=8.2 and 6.9 Hz, aromatic), 7.34 (t, 2H, J=7.5 Hz, aromatic), 5.10 (br s, 1H, NH), 3.78 (t, 2H, J=7.2 Hz, NC$\underline{H}_2$CH$_2$CH$_2$CH$_2$CH$_3$), 1.31–1.44 (m, 2H, NCH$_2$C$\underline{H}_2$CH$_2$CH$_2$CH$_3$), 1.13–1.21 (m, 4H, NCH$_2$CH$_2$C$\underline{H}_2$C$\underline{H}_3$), 0.89 (t, 3H, J=7.0 Hz, NCH$_2$CH$_2$CH$_2$CH$_2$C$\underline{H}_3$); $^{13}$C NMR (CDCl$_3$) δ 151.28, 149.25, 129.77, 129.42, 122.87, 122.65, 116.42, 50.82, 31.40, 28.95, 22.32, 13.91; Anal. Calcd for C$_{18}$H$_{20}$N$_2$ (264): C, 81.77; H, 7.62; N, 10.59. Found: C, 81.78; H, 7.82; N, 10.60.

EXAMPLE 6

Assay Methods for Detecting and Quantitating CYP450 Mediated N-Dealkylation

Stock solutions were as follows: 50 mM NADPH; 100 mM potassium phosphate buffer (pH 7.2–7.8); 1 mM substrate (i.e., 9-N-alkylaminoacridine) in DMSO or 10 µM substrate in 100 mM potassium phosphate buffer. Reaction mixtures are contained in either 3 mm pathlength cuvettes or in wells of a 96 well microtiter plate. The reaction mixture contains 4–6 pmoles (4–6×10$^{-12}$ moles) of cytochrome P450 enzyme, 1 µL of 1 mM substrate stock in DMSO or 100 µL of 10 µM substrate in 100 mM phosphate buffer (5 µM final concentration) (substrate=9-N-alkylaminoacridine). Potassium phosphate buffer (100 mM) is added to the mixture to bring the volume to 195 µL. The reaction mixtures are allowed to equilibrate to 30° C. for 1–2 minutes in the temperature controlled sample compartment of either a spectrofluorimeter or a fluorescence microplate reader. The reactions are initiated by the addition of 5 µL 50 mM NADPH (final NADPH concentration 1.25 mM).

Figure 2:
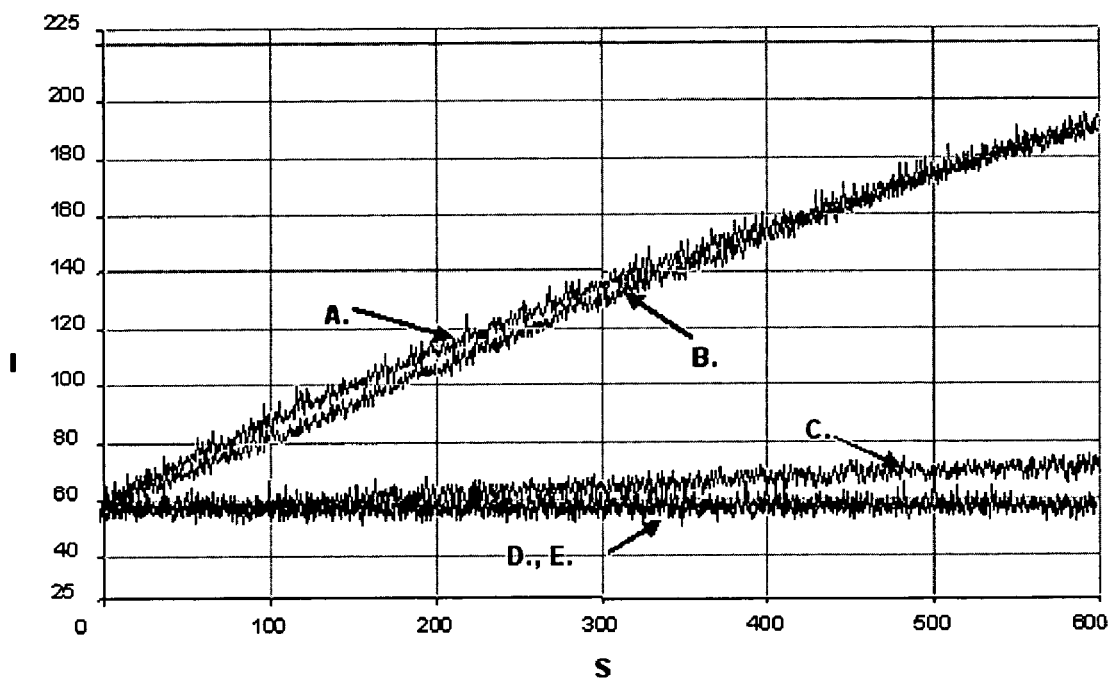
FIG. 2 is a graph showing CYP2D6 metabolism of 9-N-alkylaminoacridines. Reactions contained 8 pmoles of CYP2D6, 5 µM 9-N-alkylaminoacridine, 250 µM NADPH, in a total volume of 2 ml 100 mM potassium phosphate buffer, pH 7.2. A. 9-N-(Methylamino)acridine; B. 9-N-(Ethylamino)acridine; C. 9-N-(1-Propylamino)acridine; D. 9-N-(1-Butylamino)acridine; E. 9-N-(1-Pentylamino)acridine. I=Fluorescence Intensity; S=Seconds.

To ensure that the reaction components were thoroughly mixed the contents of the cuvette or microplate well were taken up in a micropipette and expelled back into the cuvette/microplate well. 9-Aminoacridine (product) formation was monitored by following the increase in fluorescence at 455 nm using a 402 nm excitation wavelength. The amount of 9-aminoacridine formed was calculated using a 9-aminoacridine standard curve generated for each reaction series. See FIGS. 1 and 2.

Figure 3A:
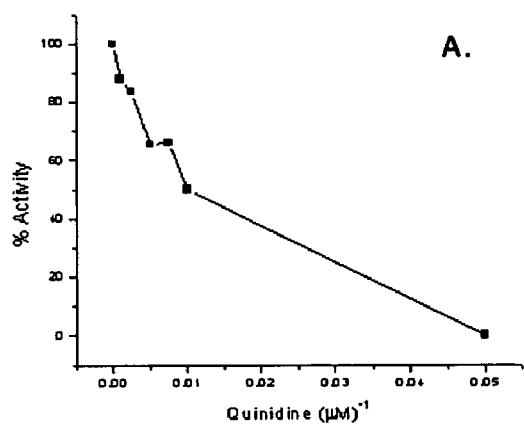
FIG. 3 is a set of graphs showing the effects of inhibitors on 9-N-(methylamino)acridine (5 µM final concentration) metabolism by CYP2D6 (5 pmoles). A. Inhibitory effects of quinidine. B. Inhibitory effects of amitryptiline (squares) and imipramine (circles).
Figure 3B:
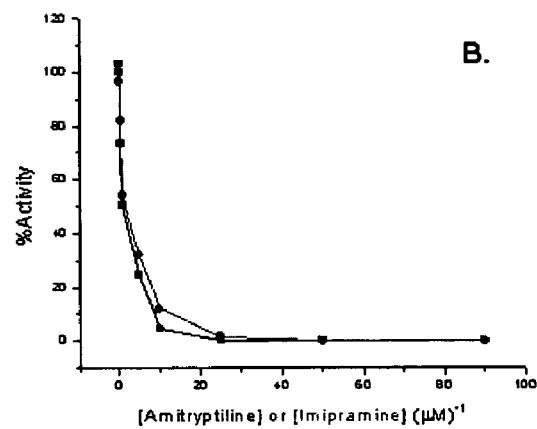

5 µM 9-N-(methylamino)acridine, CYP2D6, and various concentrations of the P450 enzyme inhibitors, quinidine, amitriptyline, and imipramine were assessed using the assay method described above. See FIG. 3. There was no preincubation period with the CYP2D6, inhibitor, and coenzyme (NADPH). Inhibitors, substrate, and enzyme were mixed. The reactions were started with NADPH and carried out for 10 minutes. Inhibitor concentrations yielding 50% inhibition ($I_{50}$) of the N-(methylamino)acridine dealkylation were as follows: quinidine—10 nM; imipramine—1 µM; amitriptyline 1 µM. These $I_{50}$ values are in the range of those reported in the literature (Yamamoto et al. 2003, Xenobiotica 33:823–839).

Assays have also been performed using subcellular fractions. Such fractions can include for example, microsomes, cellular homogenates or lysates, etc.

Liver microsomes were obtained from a variety of mammalian sources (purchased from Sigma-Aldrich, St. Louis, Mo.). These include human adult male and female, male monkey (Cynomolgus) and male Sprague-Dawley rats. All studies were performed using 9-N-(methylamino)acridine as the substrate. All sources of microsomes demonstrably metabolized the substrate to 9-aminoacridine. These studies were conducted using a spectrofluorimeter, stirred cells (10 mm pathlength), at 30° C., in a total volume of 2 ml of 100 mM potassium phosphate buffer (pH 7.2). Microsome content was 0.8 mg protein/2 ml. Substrate (9-N-(methylamino) acridine) varied from 0.1 µM–10 µM (final concentrations). Reactions were initiated with NADPH (0.25 mM final). Spectrofluorimeter settings were 405 nm excitation, 455 nm emission, excitation and emission slits 7.5 nm, and excitation and emission polarizers were horizontal and vertical, respectively. The kinetic constants are as follows:

Human liver microsomes (216 pmol cytochrome P450/reaction)
Km=17.1 µM, Vmax=0.059 pmol 9-aminoacridine/min/pmol P450

Monkey liver microsome (880 pmol cytochrome P450/reaction)
Km=18.2 uM, Vmax=0.435 pmol 9-aminoacridine/min/pmol P450

Rat liver microsomes (608 pmol cytochrome P450/reaction)
Km=20.8 nM, Vmax=0.0165 pmol 9-aminoacridine/min/pmol P450

Figure 4:
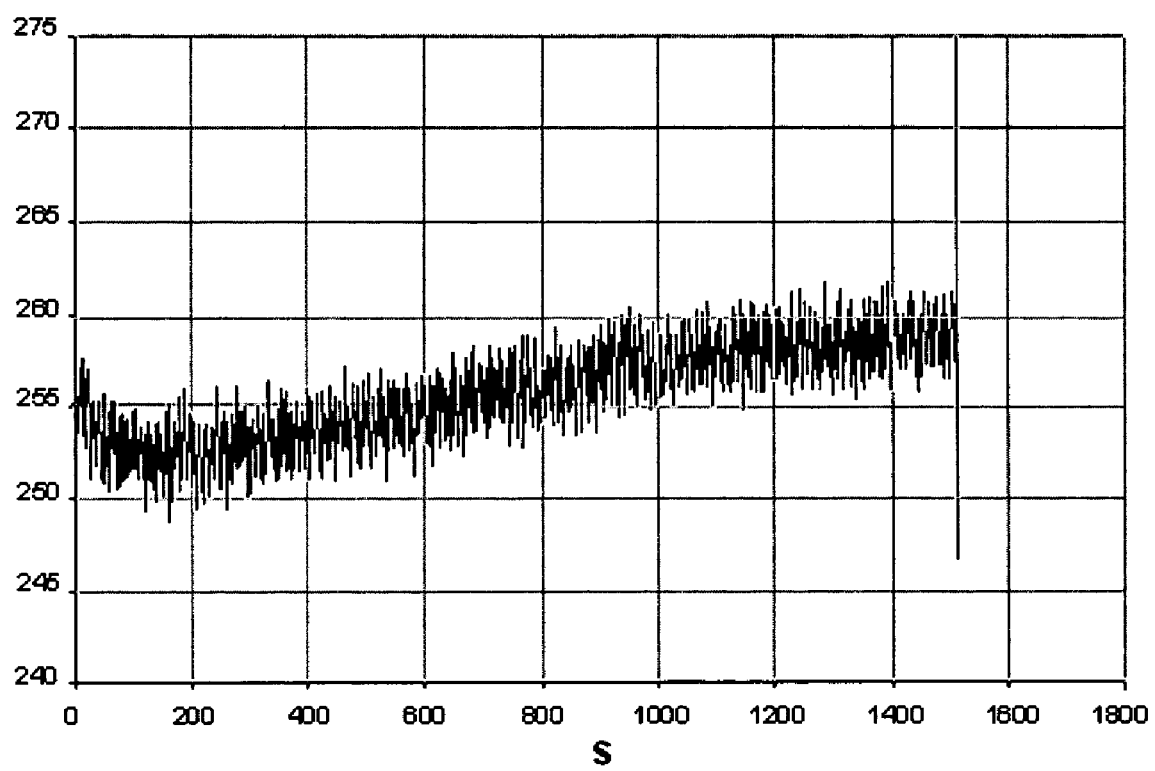
FIG. 4 is a graph showing metabolism of 9-N-(methylamino)acridine (5 µM) by human hepatocellular carcinoma (ATCC#CRL-10741) cells at 30° C. Cells were induced for four days using 25 µM Rifampin. Reactions contained ca. $1.125 \times 10^6$ hepatocytes per ml and 5 µM 9-N-(methylamino)acridine in a final volume of 2 ml Dulbecco's phosphate buffered saline, pH 7.34. Under these conditions the rate was 1.58 pmol 9-aminoacridine/20 min. I=Fluorescence Intensity, S=Seconds.

Human hepatocellular carcinoma cells (ATCC#CRL-10741) were cultured for four days with 25 µM Rifampin present in the culture medium. Culture medium containing Rifampin was changed daily. On the fifth day the cells were harvested and washed twice by centrifuging at 1000×g for 10 min and then resuspending in 2 ml of Dulbecco's phosphate buffered saline (PBS), pH 7.34. The final resuspension was in a volume of 1 ml. An aliquot (0.5 ml) of the stock suspension was added to a 10 mm pathlength fluorescence cuvette containing 1.5 ml of Dulbecco's PBS at pH 7.34, and a magnetic stirring bar. The cuvette was then placed in the spectrofluorometer's cuvette holder that was thermostatted at 30° C. and the magnetic stirrer turned on. Subsequently, 10 μL of 1 mM 9-N-methylaminoacridine (in DMSO) was added to the cuvette. The spectrofluorometer settings were the same as those used for the microsome reactions above. The reaction was initiated by addition of 10 μL 50 mM NADPH and the production of 9-aminoacridine was recorded. A typical reaction is shown in FIG. 4.

REFERENCES (1) Spatzenegger, M., and Jaeger, W. (1995) Drug Metab. Rev. 27, 397–417
(2) Murray, M. (1992) Clin. Pharmacokinet. 23, 132–146
(3) Niwa, T., Sato, R. Yabusaki, Y., Ishibashi, F., and Katagiri, M. (1999) Xenobiotica 29, 187–193
(4) Chiron, J. and Galy, J P. (2004) Synthesis 3, 313–325
(5) Crespi, C. L., Miller, V. P., and Penman, B. W. (1997) Analyt. Biochem. 248, 188–190
(6) Doostdar, H., Burke, M. D., and Mayer, R. T. (2000) Toxicology 144, 31–38

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for determining N-dealkylase activity of a cytochrome P450 enzyme comprising
   a) exposing a 9-N-alkylacridine to said enzyme under conditions suitable for catalysis to occur; and
   b) measuring fluorescence emitted by 9-aminoacridine produced by said catalysis.

2. The method as claimed in claim 1, wherein said 9-N-alkylacridine is selected from the group consisting of 9-N-(methylamino)acridine, 9-N-(ethylamino)acridine, 9-N-(1-aminopropyl)acridine, 9-N-(1-aminobutyl)acridine, and 9-N-(1-aminopentyl)acridine.

3. The method of claim 1, wherein said P450 enzyme is selected from the group consisting of CYP1A2, CYP2C8, CYPC18, CYP2C19, CYP2D6, and CYP3A4.

4. The method of claim 1, wherein said cytochrome P450 is assessed in a liver microsome preparation.

5. The method of claim 1, wherein said liver microsome is obtained from a mammal selected from the group consisting of humans, rats and monkeys.

6. The method of claim 1, wherein said method is performed in vitro in cells expressing at least one cytochrome P450 enzyme.

7. The method of claim 6, wherein said cells express a native cytochrome P450 enzyme.

8. The method of claim 6, wherein said cells express a recombinant cytochrome P450 enzyme.

9. The method of claim 6, wherein said cells are hepatocytes.

10. The method of claim 1, wherein said P450 activity is determined in a fungal cell.

11. A method of screening for agents that modulate cytochrome P450 N-dealkylase activity comprising:
   a) exposing a 9-N-dealkylacridine in the presence and absence of a test agent to cytochrome P450 under conditions suitable for catalysis to occur;
   b) measuring fluorescence emitted by 9-aminoacridine produced thereby; and
   c) determining the effect of said test agent on said fluorescence of 9-aminoacridine.

12. A method of claim 11, wherein said test agent is a drug.

* * * * *